United States Patent [19]

Armor et al.

[11] Patent Number: 5,059,713
[45] Date of Patent: * Oct. 22, 1991

[54] PROCESS FOR THE PREPARATION OF N-VINYL AMIDES

[75] Inventors: John N. Armor, Orefield; Gene E. Parris, Revere, both of Pa.

[73] Assignee: Air Products and Chemicals, Inc., Allentown, Pa.

[*] Notice: The portion of the term of this patent subsequent to Jul. 17, 2007 has been disclaimed.

[21] Appl. No.: 528,652

[22] Filed: May 24, 1990

Related U.S. Application Data

[63] Continuation-in-part of Ser. No. 211,806, Jun. 27, 1988, Pat. No. 4,942,259.

[51] Int. Cl.$^5$ .......................................... C07C 231/12
[52] U.S. Cl. ..................................... 564/187; 564/215
[58] Field of Search ................................. 564/187, 215

[56] References Cited

U.S. PATENT DOCUMENTS

| 3,377,340 | 4/1965 | Hartwimmer et al. | 564/215 |
| 3,531,471 | 9/1970 | Hartwimmer et al. | 260/239.3 |
| 3,914,304 | 10/1975 | Schnabel et al. | 260/561 R |
| 4,018,826 | 4/1977 | Glass, Jr. | 260/583 P |
| 4,322,271 | 3/1982 | Jensen et al. | 204/73 R |
| 4,334,097 | 6/1982 | Schmidt | 564/201 |
| 4,490,557 | 12/1984 | Dawson et al. | 564/159 |
| 4,554,377 | 11/1986 | Stackman et al. | 564/205 |
| 4,578,515 | 3/1986 | Dawson et al. | 564/215 |
| 4,670,591 | 6/1987 | Oftring et al. | 564/224 |
| 4,942,259 | 7/1990 | Parris et al. | 564/187 |
| 4,973,751 | 11/1990 | Dockner et al. | 564/215 |

FOREIGN PATENT DOCUMENTS 1165638 11/1969 Fed. Rep. of Germany.
60-199685 3/1985 Japan.

Primary Examiner—Richard L. Raymond
Assistant Examiner—Susan P. Treanor
Attorney, Agent, or Firm—Mark L. Rodgers; William F. Marsh; James C. Simmons

[57] ABSTRACT

N-vinyl amides having the general structural formula:

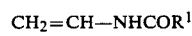

$$CH_2=CH-NHCOR^1$$

wherein $R^1$ is hydrogen, a $C_1$ to $C_6$ alkyl group or a $C_6-C_9$ aryl or substituted aryl group, are formed by cracking carboxylic acid amides having the general structure formula:

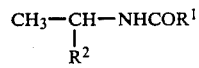

$$CH_3-\underset{\underset{R^2}{|}}{CH}-NHCOR^1$$

wherein $R^1$ is as described above, and $R^2$ is a $C_1$ to $C_9$ alkoxy, carboxy or carboxamide group. Said carboxylic acid amides are cracked by heating, to a temperature of about 210°–350° C., in the presence of a catalyst comprising MgS or an oxide or mixed oxide of Ca or Sr.

17 Claims, No Drawings

PROCESS FOR THE PREPARATION OF N-VINYL AMIDES

CROSS REFERENCE TO PARENT APPLICATION

This is a on-in-part of U.S. patent application Ser. No. 07/211,806 June 27, 1988 now U.S. Pat. No. 4,942,259 which is hereby incorporated by reference.

TECHNICAL FIELD OF THE INVENTION

The present invention relates to cracking carboxylic acid amides to form N-vinyl carboxylic acid amides.

BACKGROUND OF THE INVENTION

Several different methods have been taught in the literature to produce vinylamides. Typically these methods initially involve the formation of precursors which are subsequently pyrolyzed or cracked to yield the desired vinylamides.

U.S. Pat. No. 4,554,377 teaches a method for preparing N-vinylacetamide via the thermal pyrolysis of N-(a-methoxyethyl) acetamide at temperatures of 400° to 500° C., without using a catalyst. A similar method is taught in Japanese Patent Application 60-199685. In this method alkoxyethyl formamide derivatives are produced as precursors which are subsequently subjected to thermal decomposition to form N-vinyl formamide.

U.S. Pat. No. 4.334,097 teaches a process for the synthesis of N-vinyl amides from alkoxyethyl amides and their N-alkyl derivatives by splitting-off alcohols. The starting materials are vaporized and cracked in a furnace with porous silica at temperatures of 225°-300° C. at atmospheric or subatmospheric pressures. U.S. Pat. No. 4,322,271 describes a process in which N-vinyl-N-alkyl carboxylic acid amides are prepared by splitting-off an alcohol from the respective alkoxy precursor with or without a catalyst. The catalysts disclosed are weakly acidic catalysts, such as weakly acidic oxides of Al, Be, Zr and W; weakly acidic phosphates of Ca, Al, Mo, B and W; supported aluminosilicates in the H form., and also ammonium salts. Liquid and gas phase conditions in a temperature range of 60°-350° C. are employed.

U.S. Pat. No. 4,670,591 discloses a process for the preparation of N-a-alkoxyethylformamides, used as precursors to N-vinylformamide. The patent also discloses preparing N-vinylformamide by the pyrolysis of the precursor over catalysts such as $SiO_2$, alumina, $Al_2O_3$, marble, iron, copper, MgO or ZnO. The pyrolysis is carried out at atmospheric or subatmospheric pressure in the temperature range of 300° to 550° C.

U.S. Pat. No. 3.914,304 discloses a process for cracking N-a-alkoxyethyl carboxylic acid amides to form N-vinyl carboxylic acid amides, optionally in the presence of an inert gas such as $N_2$, Ar or $CO_2$. Filling bodies made from inert material such as glass, quartz, ceramics, porcelain, carbon, graphite, steel and the like are used to effect heat transfer in the reaction zone. Compressed oxides of zinc, zirconium, thorium, cerium, chromium, magnesium, aluminum and the like are also used. Additionally, U.S. Pat. No. 3,531,471 discloses preparing N-vinyl compounds by heating alkoxyalkyl amides at 50°-200° C. in the gaseous phase over weekly acidic catalysts such as oxides of Al, Be, Zr and W, phosphates of Ca, Al, B and W, and other similar compounds. Similar catalysts and/or processes for cracking alkoxyalkyl amides are disclosed in U.S. Pat. No. 3,377,340 and German patent application 1,165,638.

U.S. Pat. No. 4,578,515 discloses a process for cracking ethylidene bisformamide by heating it to a temperature in the range of from about 150° C. to 750° C., preferably 300° C. to 625° C., for from about 0.1 second to 1 hour in the presence of a solid surface catalyst. The pyrolysis is effected over a non-acidic or weakly acidic catalyst such as glass or marble chips. Other listed catalysts, which largely serve as heat transfer media, include diatomaceous earth, fumed silica, chopped glass fiber, silica gel, formed sand, calcium carbonate and steel. Related disclosures which describe similar pyrolysis technology to produce N-vinylacetamide or N-vinylformamide include U.S. Pat. Nos. 4,490,557 and 4,018,826.

BRIEF SUMMARY OF THE INVENTION

The present invention is a process for forming N-vinyl amides having the general structural formula:

$$CH_2 = CH = NHCOR^1$$

wherein $R^1$ is hydrogen, a $C_1$ to $C_6$ alkyl group or a $C_6$–$C_9$ aryl or substituted aryl group, by cracking; i.e. heating, carboxylic acid amides having the general structure formula:

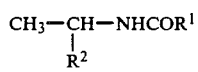

$$CH_3-CH-NHCOR^1$$
$$\phantom{CH_3-CH-}|$$
$$\phantom{CH_3-CH-}R^2$$

wherein $R^1$ is as defined above, and $R^2$ is a $C_1$ to $C_9$ alkoxy, carboxy or carboxamide group.

Such carboxylic acid amides are heated in or near the gaseous state to a temperature of about 210°–350° C. in the presence of a porous, hydrogen-abstracting catalyst selected from the group consisting of MgS and oxides or mixed oxides of Ca or Sr.

The present process achieves high conversions and high selectivities for said N-vinyl amides at relatively low temperatures at which hydrogen cyanide by-product production is low. Unlike typical prior art cracking processes, the present process can, optionally, be run at atmospheric or higher pressures, which increases the mean free path of molecules allowing more catalyst to be utilized and thereby achieving higher space/time yields relative to such other processes. Additionally, it has been demonstrated that the present process achieves good cracking results when using either single or co-feedstocks. In contract to prior art teachings on the thermal pyrolysis of vinyl amides, the present process affords higher space/time yields, lower preferred temperatures and the ability to operate at atmospheric pressure. Traditional cracking processes typically involve C—C bond breakage. The present process, however, involves the catalytic breakage of a C—X bond where X is typically compounds of O or N, or possibly F, S, P or Si. The cracking process of the present invention can be described as a vinylidine cracking reaction illustrated by the following equation:

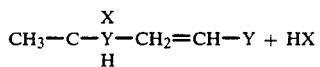

$$CH_3-\underset{H}{\overset{X}{C}}-Y-CH_2=CH-Y + HX$$

where X × O, N, S, F, P or Si

In one embodiment the present invention provides a process for cracking ethylidene bis(formamide) to form N-vinyl formamide, a monomer which is used to form a precursor polymer for the production of poly-(N-vinylamine).

DETAILED DESCRIPTION OF THE INVENTION

The present invention is a process for producing N-vinyl amides which affords substantially improved activity and/or selectivity in the cracking of carboxylic acid amides which are vinylamide precursors. Carboxylic acid amides having the general structural formula:

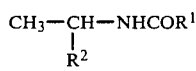

wherein $R^1$ is hydrogen, a $C_1$ to $C_6$ alkyl group or a $C_6$–$C_9$ aryl or substituted aryl group, and $R^2$ is a $C_1$ to $C_9$ alkoxy, carboxy or carboxamide group, are heated to a temperature of about 210°–350° C. in the presence of a porous, hydrogen-abstracting catalyst, to produce N-vinyl amides having the structural formula:

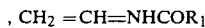

wherein $R^1$ is as described above.

Examples of specific carboxylic acid amides which are useful in this process include: ethylidene bis(formamide) (BIS), N-(l-methoxyethyl) formamide (MEF), N-(l-ethoxyethyl)formamide (EEF), N-(l-acetoxyethyl) formamide (AEF), N-(l-methoxyethyl)acetamide (MEA) and N-(l-ethoxyethyl) acetamide (EEA).

For the purpose of this invention, selectivity is defined as moles of desired product produced per moles of reactant consumed with the quotient multiplied by 100, and conversion is defined as moles of reactant consumed per moles of reactant fed with the quotient multiplied by 100. Yield is selectivity x.

The catalysts suitable for the cracking process are porous, hydrogen abstracting catalysts, selected from MgS and oxides or mixed oxides of Ca or Sr such as CaO, SrO, Sr(OH)$_2$, SrTiO$_3$ and SrO/MgO. The catalytic cracking reaction is carried out at a temperature in the range of about 210° to 350° C. Best product selectivities are obtained when the process is operated at low partial pressure of the organic feed to ensure that gas phase is predominant, since, although the reaction can take place in the liquid phase, the gas phase is preferred. Even when operating in the gas phase however, capillary condensation in the catalyst pores is typical. Total pressures in the range of about 3 torr to about 3000 torr or higher are applicable, however, total pressures up to about 1000 torr are preferred and provide the highest product selectivity. Such conditions enable rapid transport of the cracked, gaseous product to external cooling traps, where it is condensed and collected, thus preventing degradation.

Optionally, the reaction may be carried out in the presence of an inert gas diluent, such as helium, nitrogen, argon, or mixtures thereof. Such inert diluents are beneficial in that they serve to achieve low carboxylic acid amide partial pressures in the reactor, increase the heat transfer to and from the catalyst bed, decrease the mean free path of the molecules allowing better mass transport into the catalyst particles and pores, and in some instances eliminate the need for using an expensive vacuum process. The main purpose for using a diluent in the present process is to maintain a low organic amide partial pressure, whereas prior art teachings use diluents only as a sweep to prevent reactor plugging or to aid in transfer of material to the reactor. Since the inert diluent decreases the feed partial pressure of the carboxylic acid amide, the cracking reaction can be carried out at atmospheric or other pressures as indicated above and still be in the gas phase, since it is the carboxylic acid amide partial pressure which must be low in order to maintain a predominantly gas phase reaction. Preferably the inert gas is added in an amount of about 20–98 mol% based on total feed (inert and organic). While helium exhibits the best thermal conductivity, nitrogen is the least expensive and generally the preferred diluent. The use of a diluent is only a preferred embodiment however, and the reaction can be run without, although, depending on the other reaction conditions, a vacuum may be necessary to maintain a predominantly gas phase reaction. In addition, it is useful to purge the oxygen from the organic amide before the amide is fed to the catalyst. This tends to prolong catalyst life and maximize catalyst productivity.

The carboxylic acid amide to be cracked can be used in its substantially pure form, or as a crude mixture as obtained in its synthesis. Additionally, it may be diluted with a suitable functionally inert solvent, such as water, ethanol, formamide (FAM), dimethyl sulfoxide (DMSO) and the like. The reaction may be carried out in either a batch phase or continuous mode. For continuous (flow reactor) processes, residence times for the total feed is typically from about 0.01 seconds to 20 mins., while residence times of several hours can be used for batch reactors. Preferred residence times for the flow reaction, however, range from about 0.01 to about 2.0 seconds. Trace amounts of phenothiazine or similar compounds may be added to the condensed liquid products to inhibit free radical initiated reactions of the vinyl monomer product.

The following example is presented to better illustrate the present invention and is not meant to be limiting.

EXAMPLE 1

Several runs were carried out to compare the performance of the catalysts of the present invention with those of the prior art for cracking a diluted BIS in FAM feedstock under conditions of the present invention (see Table 1 footnotes). The BIS solution was deoxygenated by purging with N$_2$. 2.00cc of Harshaw MgO catalyst was loaded into a 9/16"O.D. 316ss tube with 10.0g of 10–16 mesh quartz chips pre-bed vaporizer and 7.4g as post-bed support material. The tube was assembled into a down-flow reactor and heated to 275° C. under 900 sccm He. The BIS solution was pumped to the heated reactor at a flow rate of 18.0 ml/hr and total pressure of 850 torr. The reactor effluent was cooled and samples were collected over a four hour period. 1.00g of the effluent was added to 9.00g methanol and 0.15g N-methyl pyrrolidone for quantitative analysis by gas chromatography. The specific catalysts, conditions and results are presented in Table 1 below

TABLE 1

Cracking of Dilute BIS Feed Over Catalysts in a Flow Reactor[a]

| Run | Catalyst | Temp. (°C.) | BIS Flow[b] (cc/hr) | $N_2$/He (SCCM) | Residence[c] Time (sec) | % BIS Conv. | % NVF[d] Select. |
|---|---|---|---|---|---|---|---|
| 1 | CaO | 275 | 18.00 | 900 | 0.073 | 95 | 90 |
| 2 | SrO/MgO | 275 | 18.00 | 900 | 0.073 | 95 | 89 |
| 3 | Sr(OH)$_2$ | 275 | 18.00 | 900 | 0.073 | 83 | 94 |
| 4 | SrO | 275 | 18.00 | 900 | 0.073 | 64 | 94 |
| 5 | MgS | 275 | 18.00 | 900 | 0.073 | 86 | 93 |
| 6 | SrTiO$_3$ | 275 | 18.00 | 900 | 0.073 | 78 | 90 |
| 7 | SrSnO$_3$ | 275 | 18.00 | 900 | 0.073 | 94 | 86 |
| 8 | TiO$_2$ (comparative) | 275 | 18.00 | 900 | 0.073 | 97 | 46 |
| 9 | SiO2 gel (comparative) | 275 | 18.00 | 900 | 0.073 | 86 | 62 |
| 10 | Quartz Chips (comparative) | 275 | 18.00 | 900 | 0.073 | 31 | 72 |
| 11 | Empty Tube (comparative) (no catalyst) | 275 | 18.00 | 900 | 0.073 | 26 | 60 |

[a] Reactor Pressure = 850–900 torr.
[b] Feed Composition: 20% BIS in FAM.
[c] Residence Time (sec) = (3600*P*Vb)/(N*R*T), where P and T(K) are experimental values, N is the molar hourly flow rate, Vb is the volume of catalyst as 10–16 mesh, and R is the gas constant.
[d] mole % selectivity = (moles NVF produced/moles BIS consumed)(100).

From the results reported in Table 1 above, it can be seen that the porous catalysts of the present invention are useful for cracking BIS at low temperatures; i.e. less than 350° C. It can also be seen that these catalyst are superior to the prior art catalysts for cracking BIS under these reaction conditions. Specifically, a significant increase in NVF selectivity was achieved by the catalysts of the present invention compared to those taught by Gless, et al. U.S. Pat. No. 4,018,826 (i.e. silica gel and quartz chips) and Schnabel. et al, U.S. Pat. No. 3,914,304 (i.e quartz chips), as well as using an empty tube without catalyst as also taught by Schnabel, et al.

The present invention provides an efficient, low temperature process for vinylic cracking carboxylic acid amides, especially ethylidene bis(formamide), which are vinylamide precursors, to produce N-vinyl amides such a N-vinyl formamide. The present low temperature process is advantageous in that thermal decomposition of formamide to hydrogen cyanide and water is known to occur at temperatures above or about 350° C. (see Kirk-Othmer Encyclopedia of Chemical Technology, 3rd Ed., Vol. 11, p. 258, and also Sennewald. U.S. Pat. No. 3,702,887). Consequently, the process of the present invention, greatly reduces or eliminates, the hazard of HCN production, which is a serious problem with prior, high temperature techniques. For example, analysis of reactor effluents for cyanide after various low temperature (275° C.) runs showed cyanide levels between 0.092-0.129 ppm. whereas at 400° C., cyanide levels of 149 ppm and 3750 ppm were measured for the same reaction using quartz and carbon catalysts respectively. The comparative examples above clearly show that, when run at temperatures of 210°–350° C., the present invention results in far superior conversions and/or selectivities to desired products than prior art processes, when carried out under similar conditions.

Having thus described the present invention what is now deemed appropriate for Letters Patent is set out in the following appended claims.

We claim:

1. In a process for forming N-vinyl amides having the structural formula:

$$CH_2=CH-NHCOR^1$$

wherein $R^1$ is hydrogen, a $C_1$ to $C_6$ alkyl group or a $C_6$-$C_9$ aryl or substituted aryl group, by heating to a temperature of about 210°–350° C., carboxylic acid amides having the structural formula:

$$CH_3-CH-NHCOR^1$$
$$\quad\quad\;\; |$$
$$\quad\quad\;\; R^2$$

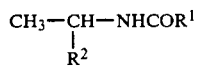

wherein $R^1$ is defined above, and
$R^2$ is a $C_1$ to $C_9$ alkoxy, carboxy or carboxamide group, the improvement for achieving higher conversions and/or selectivities for said N-vinyl amides which comprises:
heating said carboxylic acid amides in the presence of a porous catalyst which is MgS, CaO, SrO, Sr(OH)$_2$, SrTiO$_2$, SrSnO$_3$, or SrO/MgO.

2. A process in accordance with claim 1 wherein ethylidene bis(formamide) is heated to form N-vinyl formamide.

3. A process in accordance with claim 1 wherein an inert gas is used as a diluent to establish low partial pressure of the organic amide during the vinylic catalytic cracking of the carboxylic acid amides.

4. A process in accordance with claim 3 wherein said inert gas is selected from the group consisting of $N_2$, He and Ar.

5. A process in accordance with claim 3 wherein said inert gas is present in an amount of 20-98 mole % based on feed.

6. A process in accordance with claim 1 wherein said process is carried out at a pressure range of about 3 torr to about 3000 torr.

7. A process in accordance with claim 6 wherein said process is carried out at a pressure of 3 torr to 1000 torr.

8. A process in accordance with claim 1 wherein $R^1$ is H.

9. A process in accordance with claim 1 wherein the carboxylic acid amide is selected from the group consisting of: ethylidene bis(formamide), N-(l-ethoxyethyl)-formamide, N-(l-acetoxyethyl)formamide, N-(l-ethoxyethyl)acetamide, N-(l-methoxyethyl)formamide and N-(l-methoxyethyl)acetamide.

10. A process in accordance with claim 1 wherein the carboxylic acid amide is mixed with a functionally inert solvent.

11. A process in accordance with claim 10 wherein said inert solvent is selected from the group consisting of water, ethanol and formamide.

12. A process in accordance with claim 1 wherein said process is carried out as a batch process.

13. A process in accordance with claim 1 wherein said process is carried out as a continuous process in a flow reactor.

14. A process in accordance with claim 1 wherein said process is carried out primarily in the gas phase.

15. A process in accordance with claim 1 wherein said process is carried out at subatmospheric pressure using a vacuum.

16. A process in accordance with claim 1 wherein said process is carried out at atmospheric pressure.

17. A process in accordance with claim 1 wherein oxygen is purged from the organic amide before the amide is fed to the catalyst.

* * * * *

UNITED STATES PATENT AND TRADEMARK OFFICE
CERTIFICATE OF CORRECTION

PATENT NO. : 5,059,713

DATED : October 22, 1991

INVENTOR(S) : John N. Armor, et al

It is certified that error appears in the above-identified patent and that said Letters Patent is hereby corrected as shown below:

Column 5, Line 68
    Delete "CH=NH" and substitute therefor - - CH-NH - -

Signed and Sealed this

Twenty-sixth Day of October, 1993

Attest:

BRUCE LEHMAN

Attesting Officer     Commissioner of Patents and Trademarks